US006524331B1

United States Patent
Kohout et al.

(10) Patent No.: US 6,524,331 B1
(45) Date of Patent: Feb. 25, 2003

(54) THERMAL DEVICE WITH AUTOMATIC NESTING FEATURE

(75) Inventors: Daniel Kohout, Grayslake, IL (US); Charles Ray Mason, Moberly, MO (US); Michael Fleck, Moberly, MO (US); E. Ron Phipps, Columbia, MO (US); Tim Shaneberger, Columbia, MO (US); Everett Posey, Jacksonville, TX (US); Gregory Groenke, Gurnee, IL (US)

(73) Assignee: Allegiance Corporation, McGaw Park, IL (US)

( * ) Notice: Subject to any disclaimer, the term of this patent is extended or adjusted under 35 U.S.C. 154(b) by 0 days.

(21) Appl. No.: 09/566,543

(22) Filed: May 8, 2000

Related U.S. Application Data (63) Continuation-in-part of application No. 09/156,418, filed on Sep. 18, 1998, now abandoned.

(51) Int. Cl.[7] .................................................. A61F 7/00
(52) U.S. Cl. .............................. 607/96; 607/114; 5/603; 5/421; 5/945
(58) Field of Search ................................. 607/114, 108, 607/96; 5/603, 421, 422, 945

(56) References Cited

U.S. PATENT DOCUMENTS

| | | | | |
|---|---|---|---|---|
| 3,089,153 A | * | 5/1963 | Bosc ...................... 297/DIG. 3 |
| 3,854,156 A | * | 12/1974 | Williams .................... 126/204 |
| 3,913,559 A | | 10/1975 | Dandliker ................... 126/263 |
| 3,951,127 A | * | 4/1976 | Watson et al. .............. 126/204 |
| 4,056,858 A | | 11/1977 | Weber .......................... 5/365 |
| 4,331,556 A | | 5/1982 | Arrhenius ................. 252/363.5 |
| 4,382,446 A | | 5/1983 | Truelock et al. ............ 128/402 |
| 4,391,267 A | | 7/1983 | Arrhenius ................... 126/400 |
| 4,404,820 A | * | 9/1983 | Romaine .................... 215/12.2 |
| 4,596,250 A | * | 6/1986 | Beisang et al. ............. 607/114 |
| 4,856,651 A | | 8/1989 | Francis, Jr. ................. 206/219 |
| 4,872,442 A | | 10/1989 | Manker ..................... 126/263 |
| 4,886,063 A | | 12/1989 | Crews ........................ 128/403 |
| 4,964,183 A | * | 10/1990 | LaForce, Jr. .................. 4/538 |
| 4,986,076 A | | 1/1991 | Kirk et al. ........................ 62/4 |
| 5,129,391 A | | 7/1992 | Brodsky et al. ............ 128/380 |
| D357,589 S | * | 4/1995 | Langhammer et al. ....... D6/333 |
| 5,441,534 A | | 8/1995 | MacWinnie et al. ........ 607/108 |
| 5,476,490 A | | 12/1995 | Silver ......................... 607/108 |
| 5,545,197 A | | 8/1996 | Bowen ....................... 607/108 |
| 5,674,269 A | * | 10/1997 | Augustine ................... 607/107 |
| 5,791,223 A | | 8/1998 | Walters ................. 126/263.03 |
| 5,916,088 A | * | 6/1999 | Gueli ......................... 224/616 |
| 5,948,013 A | * | 9/1999 | Swezey et al. ................ 5/636 |
| 6,277,144 B1 | * | 8/2001 | Tomic-Edgar et al. ...... 607/108 |

OTHER PUBLICATIONS

"International award–winning student invention benefits newborns" by Jamie Lawson Reeves in *The Vanderbilt Register*, Jan. 19–25, 1998, p. 4.
"New Style Mattress Like Womb for Baby" by Julie Appleby in *Contra Costa Times Newspaper* (Sep. 14, 1996).
"The Safety of Partial Intrauterine Analogue Transition Environments: A Literature Review and Discussion" in *Neonatal Intensive Care*, Sep./Oct. 1992.
"Infants Who Sleep on Used Mattresses Reportedly have a Higher Risk of SIDS" in *Medical Tribune*, Jul. 17, 1997.

* cited by examiner

*Primary Examiner*—Linda C. M. Dvorak
*Assistant Examiner*—Jocelyn Ram
(74) *Attorney, Agent, or Firm*—Andrew G. Rozycki (57) ABSTRACT

The invention disclosed herein relates to a device for applying thermal therapy, treatment or comfort to a patient or user which includes a container having an upper side and lower side with a space therebetween containing a chemical composition adapted to provide a thermal effect, and a plurality of discrete attachment areas which generally define a central location in the container. The device has a nest configuration and automatically conforms to the user's geometry upon application of weight thereon. The discrete attachment areas are positioned to define an inner peripheral base portion and outer peripheral portion in the device which collectively form the nest configuration. The device is particularly useful in thermal treatment for infants.

37 Claims, 6 Drawing Sheets

THERMAL DEVICE WITH AUTOMATIC NESTING FEATURE

CROSS-REFERENCE TO RELATED APPLICATIONS

This application is a continuation-in-part of U.S. Ser. No. 09/156,418 filed Sep. 18, 1998, now abandoned.

FIELD OF THE INVENTION

The invention relates generally to thermal devices. In particular, the invention relates to infant warming mattresses using chemically induced thermal reactions.

BACKGROUND OF THE INVENTION

Various forms of thermal therapy have been used to provide either heating or cooling application temperatures to specific parts of the patient's body. For example, heat has been used to increase blood flow and speed the healing process to an injured area of the body. Similarly, cooling has been used to prevent swelling and reduce pain in an injured area of the body.

Hot and cold packs are well-known to be useful in a variety of applications. Representative thermal packs are described in U.S. Pat. No. 4,856,651 to Francis, Jr., for example. Of particular interest is the use of a warming pad to maintain proper body temperatures for neonatal, pediatric and geriatric patients. Infants, for example, are thermally treated by placing them on a heated mattress. Several types of such mattresses are currently available. One such mattress, the Porta-Warm™ mattress (available from Allegiance Healthcare Corp. McGaw Park, Ill.), is made using a single sheet of film with non-woven material folded over itself to create a rectangular shape which is sealed around the edges. Within the pouch are a series of seals which extend across the pouch to form a plurality of rectangular compartments. Within each compartment is at least one bubble containing a thermal chemical solution of sodium thiosulfate, dextrose and water. When the thermal solution is activated, heat is released in a controlled manner for a period of approximately two hours.

Other currently available thermal mattresses include those made of a single pouch without subdivisions and having a thermal solution contained in a pouch which releases heat upon activation. For example, U.S. Pat. No. 3,951,127 to Watson et al. discloses a thermal infant mattress wherein two sealed sheets are maintained in a contiguous relationship at a plurality of points. Another type of mattress, which is currently available from Infant Advantage Inc. (San Ramone, Calif.), has a flat, rectangular shape and has additional padding on top of the mattress to create a conformable structure. However, neither the padding nor the mattress contain chemical reactants to provide heat.

There is a need for thermal devices having improved functions and configurations and which afford enhanced therapeutic or comfort benefit for the user.

SUMMARY OF THE INVENTION

The invention disclosed herein is a device for applying thermal therapy, treatment or comfort to a patient or user which includes a containment having an upper side and lower side with a space therebetween containing a chemical composition adapted to provide a thermal effect (either exothermic or endothermic), and a plurality of discrete attachment areas which generally define a central location in the container. The device has a nest configuration and automatically conforms to the user's geometry upon application of weight thereon. The discrete attachment areas are positioned to define an inner peripheral base portion and outer peripheral portion in the device which collectively form the nest configuration. The device is particularly useful in providing thermal therapy, treatment or comfort for infants.

Accordingly, there is disclosed a device for providing thermal therapy comprising:
 a) a containment having upper and lower sides and space therebetween;
 b) a chemical composition adapted to provide a thermal effect contained within said space;
 c) a plurality of discrete attachment areas connecting the upper and lower sides within the perimeter of the device, said attachment areas being centrally located so as to define an inner peripheral base portion and outer peripheral portion of the device; and wherein the device has a nest configuration and is adapted to conform to a body upon application of weight thereon.

The chemical composition adapted to provide a thermal effect used in the device can be any composition or combination of ingredients adapted to create a thermal effect in a controllable manner and provide an amount of fluid within the containment sufficient to afford conformability of the device to the body. In one embodiment, the ingredients of the chemical composition are physically separated until use of the device, at which time the ingredients are combined and reacted to produce the thermal effect. Preferably, the chemical composition used in the invention is exothermic and thereby produce a warming effect.

One advantage of the device of the invention is that it permits the application of thermal therapy in conformance with the patient's own physical geometry by accommodating the application of weight without adversely affecting the effectiveness or function of the device during its use. Accordingly, the device provides an improved thermal therapy to the patient. Another advantage of the device is that in addition to the geometrical accommodation of the device to the patient, the internal flow of fluid within the device is unrestricted by the discrete attachment areas, thereby enabling rapid conformation of the device to the patient's body. Yet another advantage is that the nest configuration provides a relatively comfortable place for an infant to rest and can assist in maintaining the infant in a generally constant position.

DETAILED DESCRIPTION OF THE INVENTION

As used herein, the term "device" is meant to indicate the collective embodiment of the various components and features as described herein for the invention, such as the containment, chemical composition, discrete attachment areas, and the like. The term "containment" is meant to refer to the portion of the device which houses the chemical composition according to the invention.

The term "discrete" when used in reference to attachment areas of the invention is meant to describe a individually distinct, separate and non-contiguous attachment which is remotely positioned from at least one other such attachment such that no pockets, chambers, or otherwise separated portions are formed within the containment. The term "plurality" is meant to indicate a number of two or more.

The term "controllable" when used in reference to the chemical composition is meant to indicate a chemical composition which can be manipulated (by selection of ingredient(s) and/or proportions thereof) to provide a specific temperature for a specific time period to render an anticipated thermal effect.

The term "nest" when used in reference to the configuration of the device is meant to describe a structure having generally defined central and peripheral portions such that the peripheral portion can be raised relative to the central portion when weight is applied to the central portion.

The terms "patient" and "user" are used interchangeably and are both meant to include any one who can benefit from or appreciate the use of the device. The terms include an infant.

The terms "therapy," "treatment," and "comfort" used in reference to the term thermal are used interchangeably and are meant to indicate receipt of the thermal effect as afforded by the device of the invention. Such therapy, treatment or comfort may or may not necessarily be associated with medical treatment pursuant to an injury or disorder.

Figure 1:
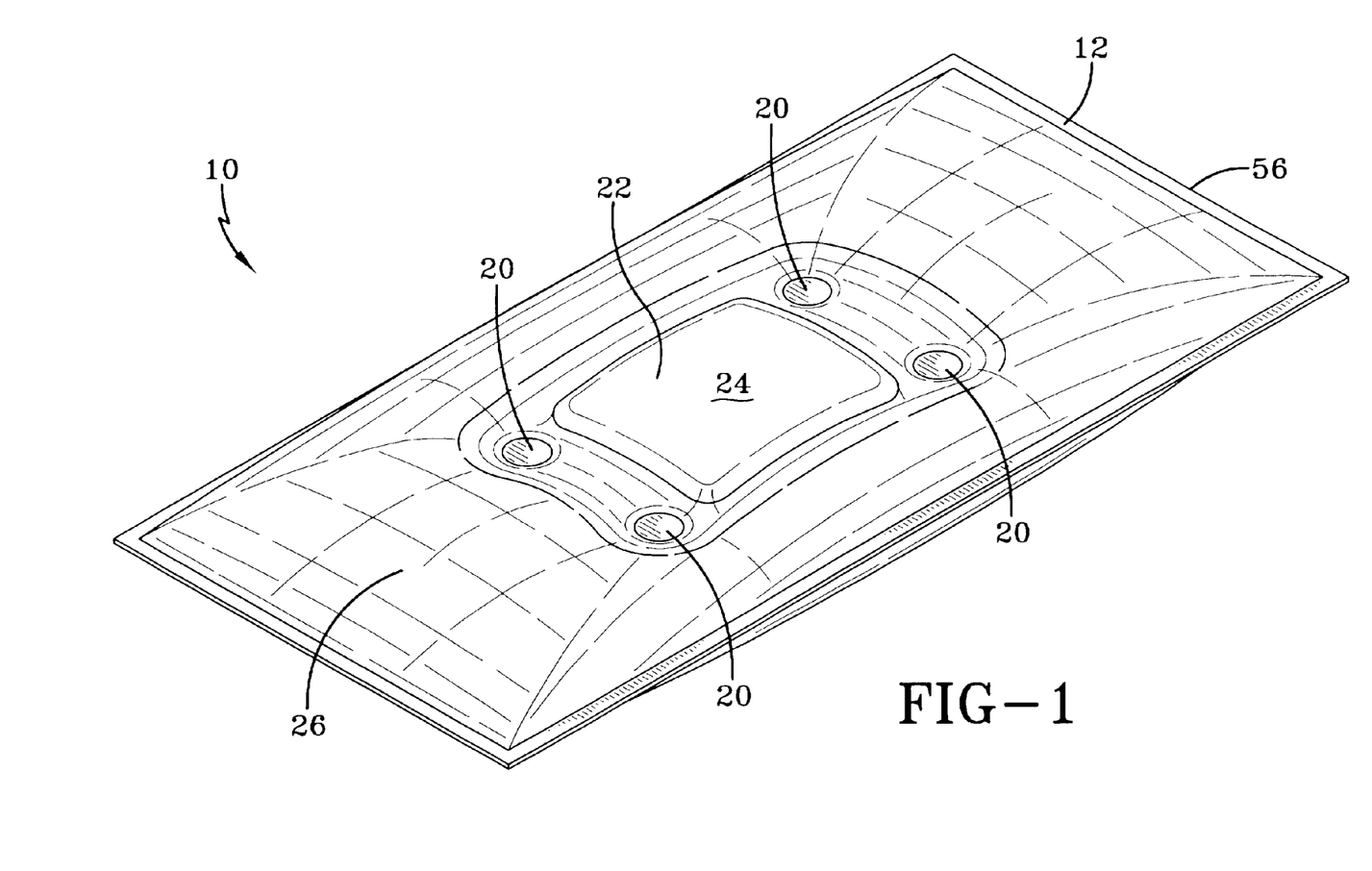
FIG. 1 is an overall perspective view of the device according to one embodiment of the invention.
Figure 2:
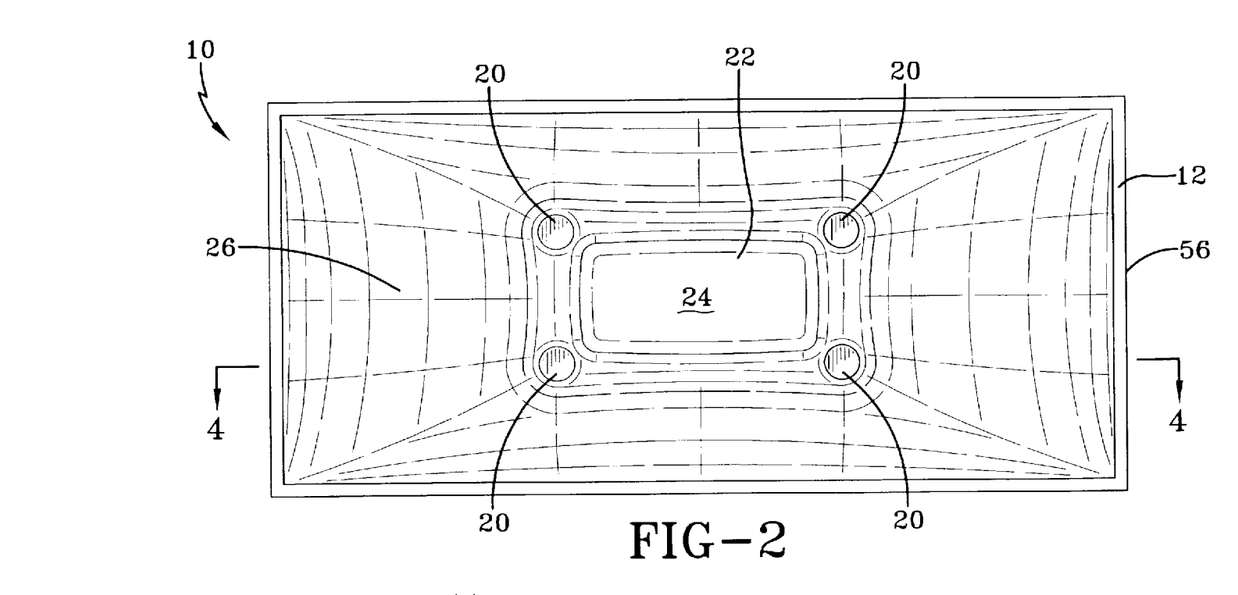
FIG. 2 is a top view of the device according to one embodiment of the invention.
Figure 3:
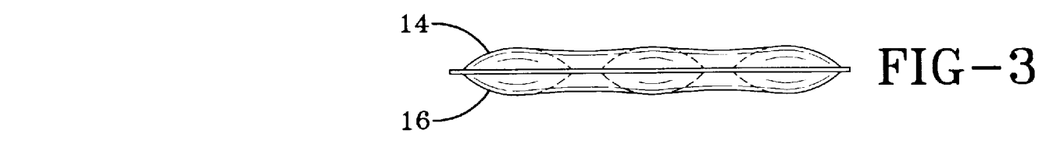
FIG. 3 is an end view of the device according to one embodiment of the invention.
Figure 4:
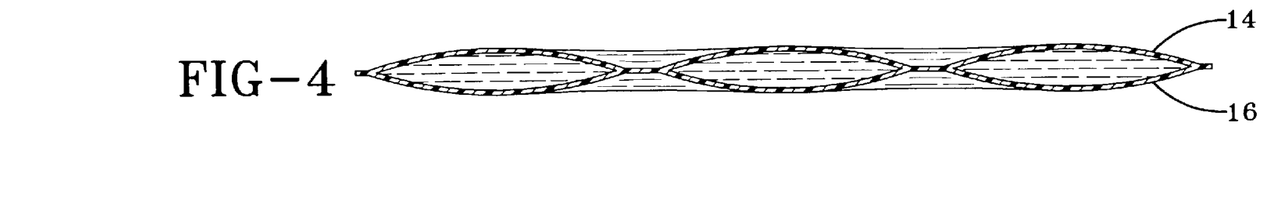
FIG. 4 is a side view of the device according to one embodiment of the invention.

As depicted in the figures, one embodiment of the device 10 for providing thermal treatment according to the invention generally comprises a containment 12 having upper and lower sides 14 and 16 respectively (see FIGS. 3 and 4) and space therebetween; a chemical composition adapted for providing a thermal effect contained within said space; a plurality of discrete attachment areas 20 connecting the upper and lower sides 14 and 16 within the perimeter of the device, said attachment areas being centrally located so as to define an inner peripheral base portion 22 and outer peripheral portion 26 of the device; and wherein the device has a nest configuration 24 and is adapted to conform to a patient's body upon application of weight thereon. In one embodiment, the device 10 can have an overall configuration of a mattress as shown in the figures.

The containment 12 having upper and lower sides can be composed of any flexible material which is impervious to fluid. Preferably, the material can withstand the internal pressure exerted on the material as a result of placement of weight upon the device in accordance with its anticipated use. Typically, the containment material comprises a polymeric material in the form of a sheet or film. Examples of suitable polymeric materials include, but are not limited to, polyethylene, polyester, nylon, vinyl, and the like. As shown in the figures, the containment 12 is completely sealed around the periphery 56 of the device 10. Sealing of the upper and lower sides of the containment can be accomplished using any well known technique in the art, such as chemical adhesion, thermal melting techniques, radiofrequency welding techniques, and the like.

Figure 5A:
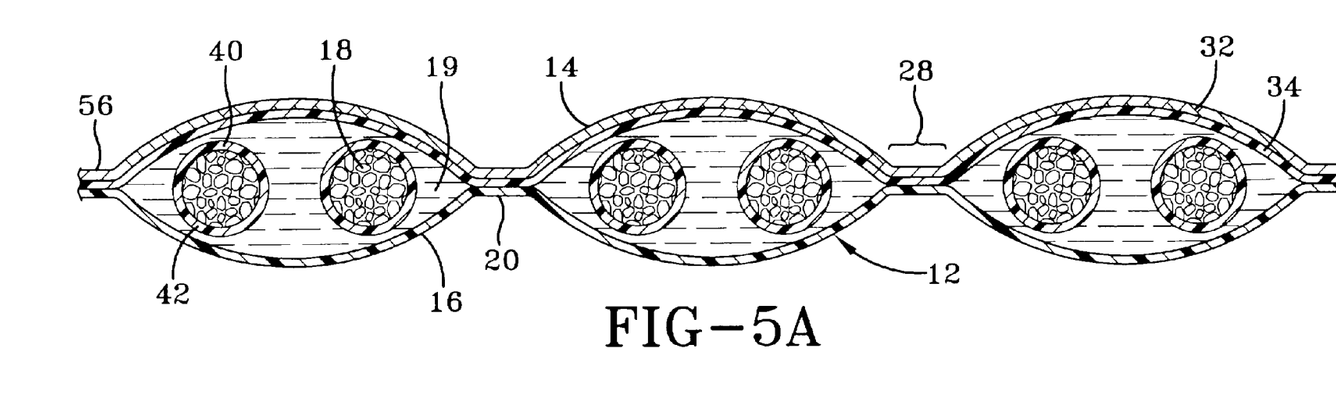
FIGS. 5A and 5B are cross-sectional views of the device taken along line AA as shown in FIG. 2, showing two different chemical composition configurations according to one embodiment of the invention.

In a further embodiment, one or more surface layers can be laminated to the containment material. For example, a layer of softer, non-abrasive material 32 can be laminated to the polymeric containment material 34 as shown in FIG. 5A. When the device is used for infants, it is preferred that the material used for either the containment or surface layer or both is one which is non-abrasive to an infant's skin.

A variety of material types and combinations thereof can be used. For example, the containment material can further comprise a material support structure, such as reinforcing fibers, within the material. The containment material can be opaque, semi-transparent or transparent thereby enabling viewing of the internal contents of the device. The entire containment can be composed of a single type of material, or alternatively, different materials or combinations of containment materials can be used for the upper and lower sides of the device. For example, the upper side can contain a softer, non-abrasive material and the lower part can contain a more puncture-resistant material. In a further embodiment, the containment itself can be composed of a single layer of material or multiple layers of material.

Variations in number, position, size and shape of the discrete attachment areas are possible in accordance with the invention, provided the attachment areas are centrally located and define an inner peripheral base portion and outer peripheral portion of the device. Generally, the discrete attachment areas make up a minority of the surface area of the upper and lower sides of the device. Typically, the discrete attachment areas make up less than about 10% of the surface area. More typically, the attachment areas make up less than about 3% of the surface area of the upper and lower sides.

The discrete attachment areas can be any shape which permits liberal flow of the fluid throughout the interior of the containment between the inner peripheral base portion and the outer peripheral portion of the device in accordance with the invention. In one embodiment, the discrete attachment areas 20 can be circular in shape (as illustrated in the Figures). The discrete attachment areas can be formed using any technique known in the art for physically connecting discrete portions 28 of the upper and lower sides 14 and 16 (see FIGS. 5A and 5B). Suitable physical connection techniques which can be used include, but are not limited to, sealing techniques such as heat sealing, ultrasonic sealing, and chemical adhesion.

In a preferred embodiment, at least four centrally located discrete attachment areas are used in the device to define the inner peripheral base portion and outer peripheral portion, wherein the discrete attachment areas are positioned only in the area between the inner peripheral base portion and outer peripheral portion. Even more preferred are four centrally located discrete attachment areas defining an inner peripheral base portion wherein the attachment areas are arranged to define a square or rectangular inner periphery. In the case of an infant warming device, the dimensions of the central location as defined by the discrete attachment areas has a length and/or width that is less than that of an infant to be placed thereon.

The plurality of discrete attachment areas function to connect the upper and lower sides of the containment in a central location and to produce a nest structure while permitting the unrestricted flow of fluid within the device upon application of weight thereon.

The overall dimensions and shape of the device per se can vary according to the invention. Accordingly, the device can have an ovoid, circular, square, or rectangular shape, and the like. In the case of a device intended for infants, e.g., infant warming device, the dimensions of the device, i.e., the length, width, thickness, accommodate the size of the infant to be placed thereon. In one embodiment, the device comprises an overall rectangular shape, e.g., mattress, and comprises four centrally positioned discrete attachment areas defining a rectangular or square inner peripheral base portion as seen in the figures.

The chemical composition adapted to provide a thermal effect used in the device can be any composition (e.g., combination of ingredients) adapted to create a thermal effect in a controllable manner and provide an amount of fluid within the containment sufficient to afford conformability of the device to the user's body. In one embodiment, the ingredients of the chemical composition are physically separated until use of the device, at which time the ingredients are combined and reacted to produce the thermal effect. The thermal reaction can be either cooling or exothermic (heat generating). Preferably, the chemical composition used in the invention is exothermic and thereby produces a warming effect.

Suitable chemical compositions which can be used in the invention include, but are not limited to, phase change formulations, solute with solvent combinations, and thermal fluids. Examples of phase change formulations which can be used include, but are not limited to, those comprising sodium thiosulphate pentahydrate (STP) with STP and borax crystals; sodium acetate trihydrate (SAT) with SAT crystals; sodium acetate trihydrate with metallic activators; and STP and SAT with STP and SAT crystals. Metallic activators (or initiators) which initiate thermal reactions include those disclosed in U.S. Pat. No. 4,872,442 to Manker, the entire disclosure of which is incorporated herein by reference. Solute with solvent combinations which can be used include, but are not limited to, combinations comprising water with a chemical activator selected from the group consisting of potassium permanganate, calcium chloride, magnesium sulfate, calcium magnesium sulfate, and sodium acetate, and combinations thereof. Thermal fluids which can be used include single, unitary compositions adapted to release or absorb thermal energy, such as thermal gels. Suitable thermal gels can comprise water and a hydrophilic polymer selected from the group consisting of hydrogels, starches, cellulosics, and silica gels, and combinations thereof.

Figure 5B:
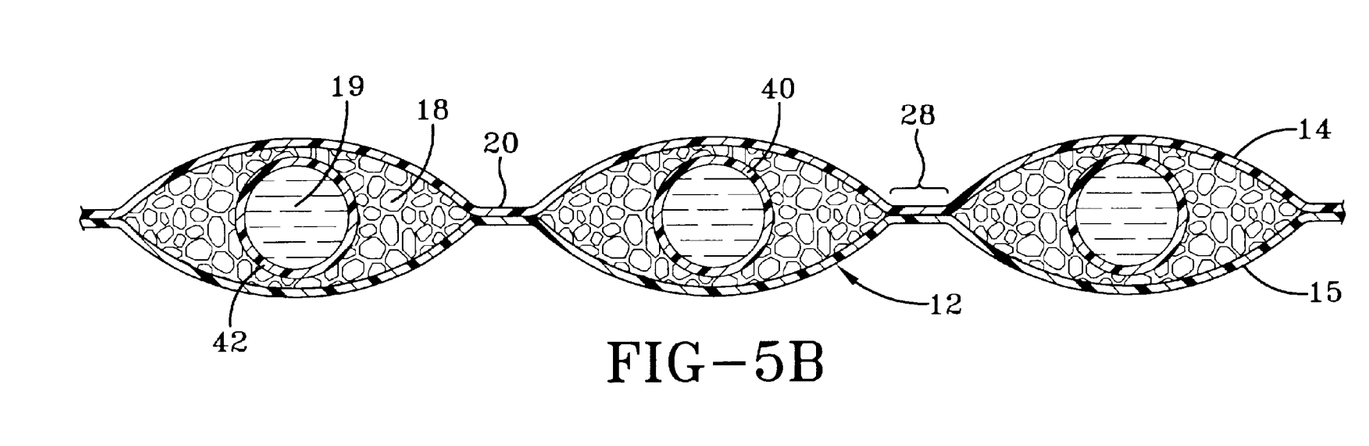
Figure 7:
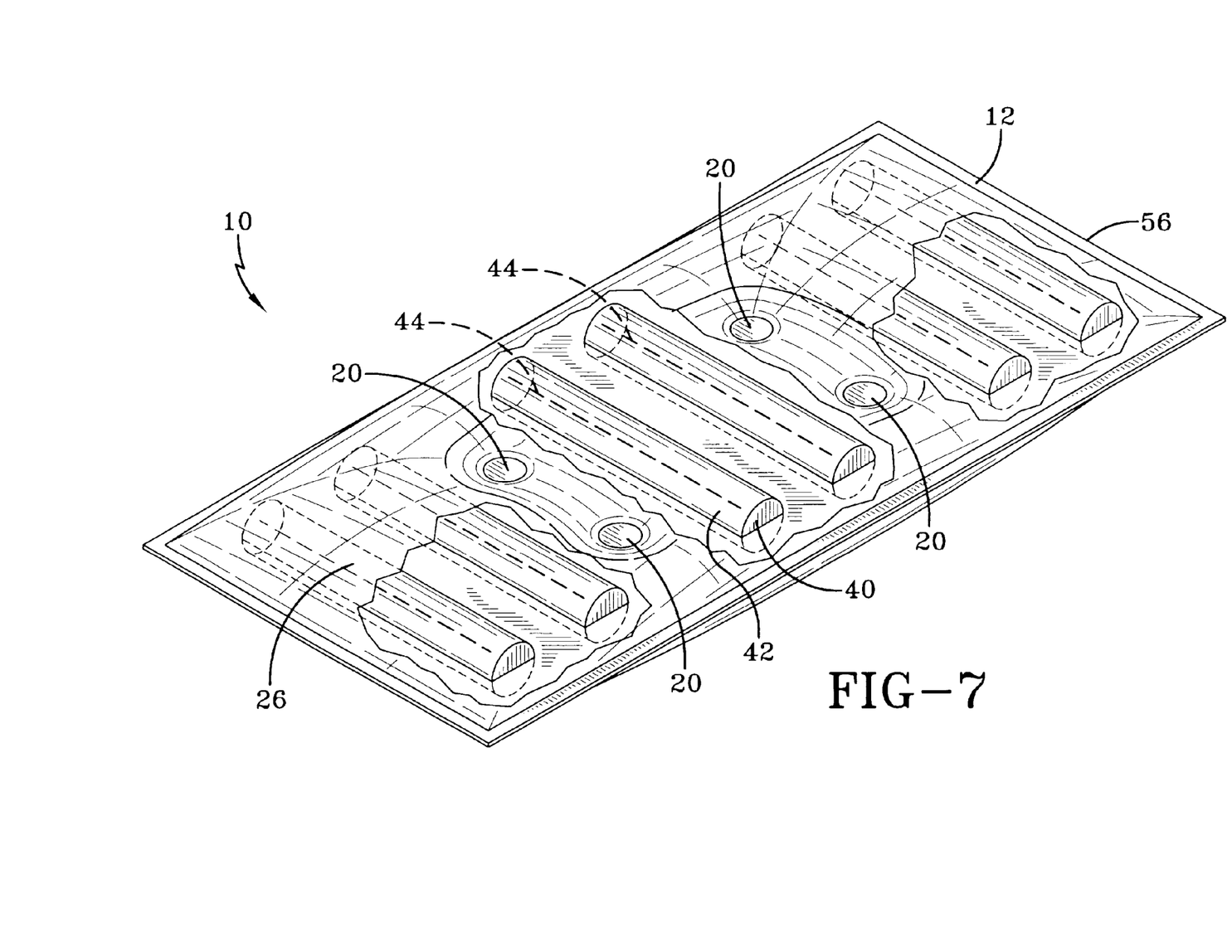
FIG. 7 is a cut-away perspective of the device showing pouches for the chemical composition ingredients positioned within the device according to one embodiment of the invention.

A variety of physical separation structures or arrangements can be used with the invention. Some of such physical separation structures are illustrated in FIGS. 5A, 5B and 7. For example, a solid ingredient can be contained within a pouch and a liquid ingredient can be surrounding the pouch within the interior to the containment as shown in FIG. 5A. Alternatively, a liquid ingredient can be contained within a pouch and a solid ingredient is located outside of the pouch within the containment as seen in FIG. 5B. Two separated liquid ingredients can also be located within the containment of the device.

In one embodiment for physical separation of ingredients and as depicted in FIGS. 5A, 5B and 7, at least one of the ingredients of the composition can be contained within at least one rupturable pouch 40 or bubble within the containment of the device. The rupturing of the pouch 40 (or bubble) brings ingredients 18 and 19, one of which was contained in a pouch, into contact with the other ingredient. The combination of the two ingredients of the chemical composition together to form a mixture creating the thermal reaction and, thus, the thermal effect. The mixture is then permitted to flow unrestricted throughout the interior of the device.

The material 42 used to physically separate the ingredients of the chemical composition (e.g., the pouch or bubble material) can be any material known in the art which can rupture with applied force, including but not limited to, polymeric materials. Examples of suitable polymeric materials include polyethylene, polyester, combinations of polyester and polyethylene, mylar (polyester and metallic materials), and the like. Pouches used in the device can further contain rupture facilitating features as well, such as perforations or seams 44 (as seen in FIG. 7) or otherwise weakened areas which break upon application of force.

The shape, number and arrangement of pouches in the device can vary according to design preferences or the user' preferences or needs. At least one pouch can be positioned within the central portion of the device or, alternatively, at least one pouch can be positioned within the peripheral portion of the device, or both. In the embodiment shown in FIG. 7, a plurality of longitudinal pouches 40 are laterally positioned within the device in a substantially even distribution pattern within both the inner peripheral base portion 22 and outer peripheral portion 26 of the device.

Figure 6:
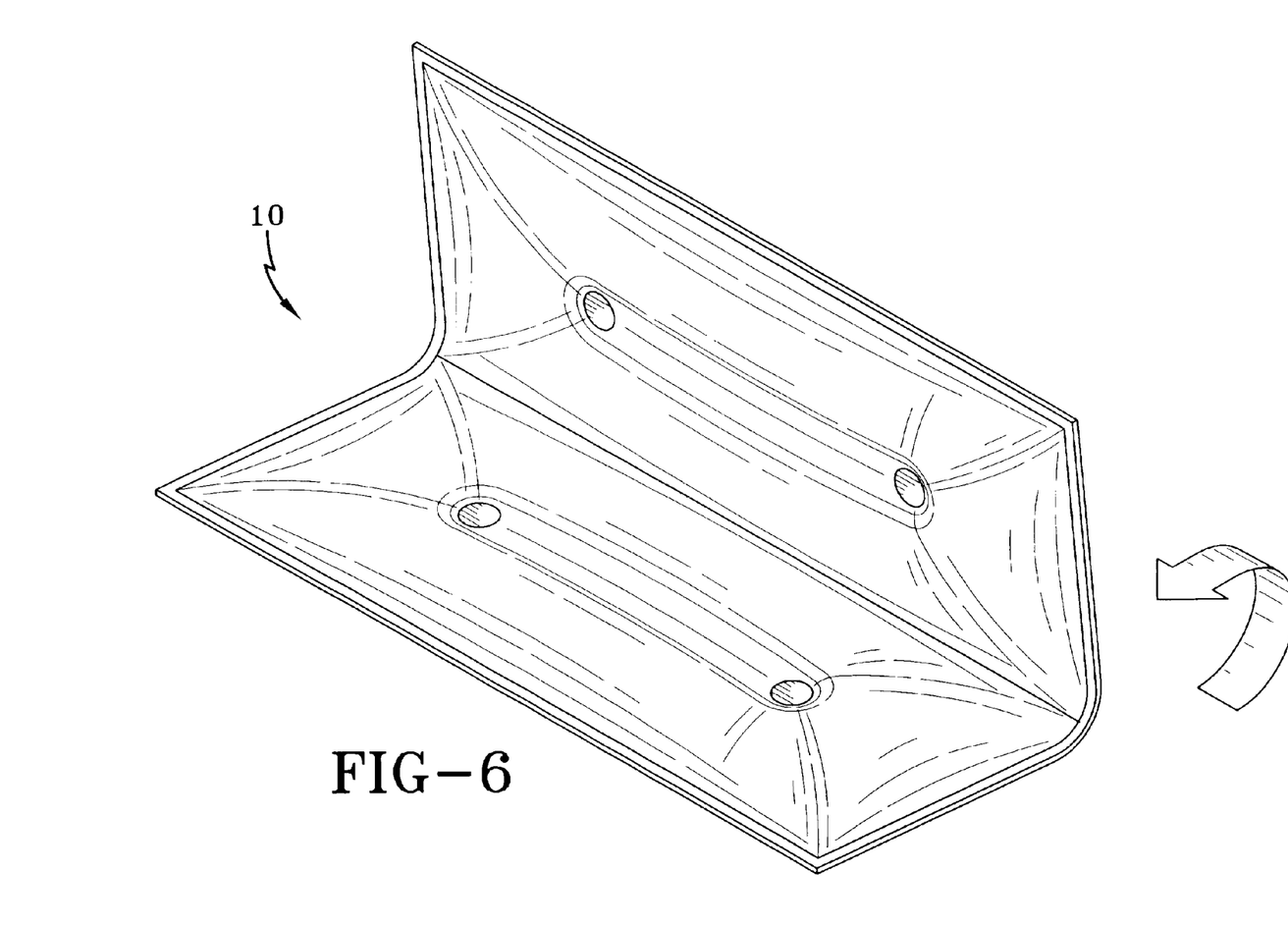
FIG. 6 is an illustration of the preparation of the device prior to use according to one embodiment of the invention.

The pouches 40 containing one of the ingredients 18 of the composition are physically ruptured upon application of force thereto. The type of force needed to rupture the pouch will vary according to the pouch design. FIG. 6 illustrates one embodiment of the device wherein the device contains a plurality of elongated pouches as seen in FIG. 7 which upon folding the device along an axis transverse to at least one pouch ruptures the pouch to combine the ingredients and initiate the thermal reaction.

Figure 8:
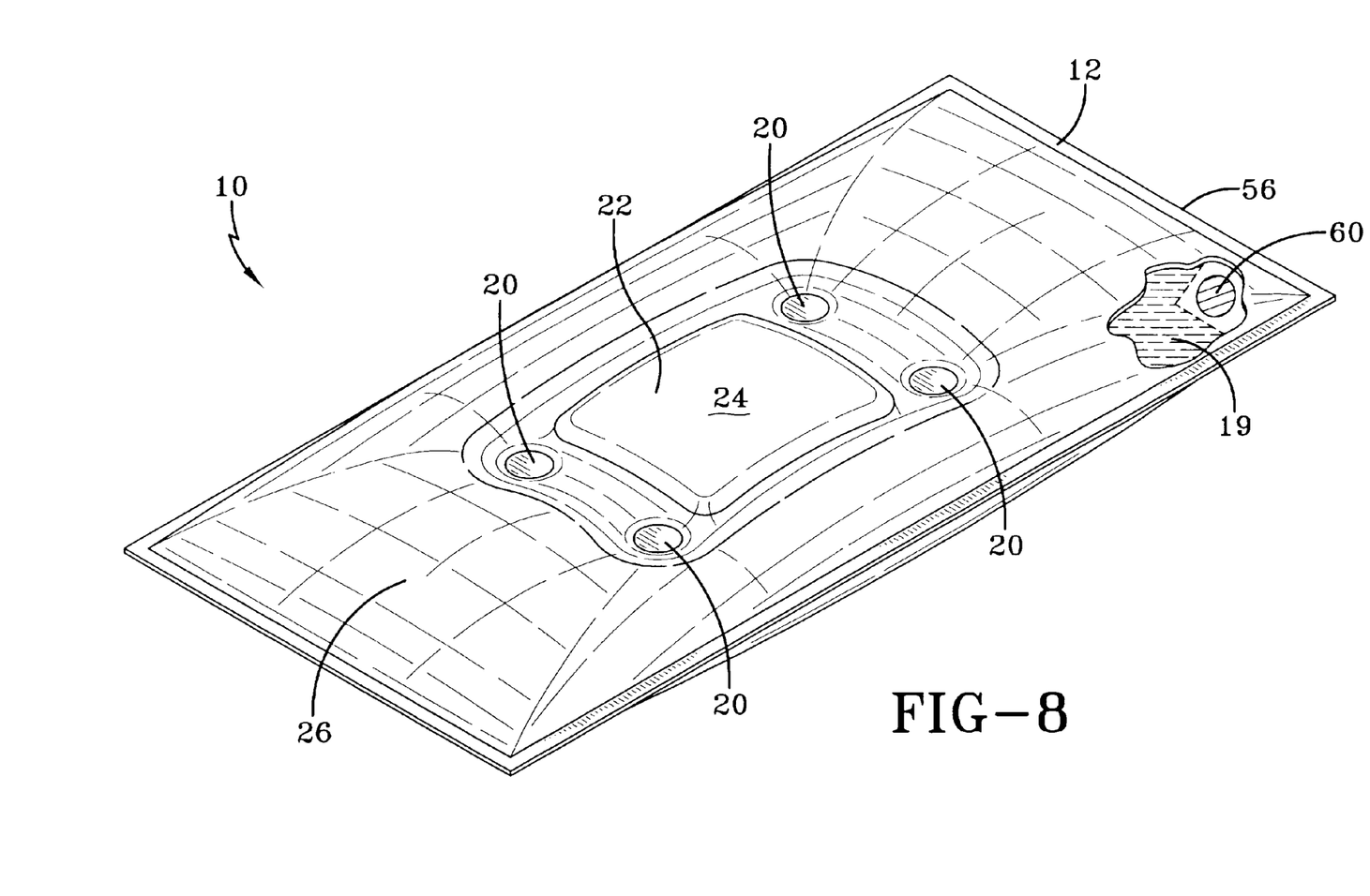
FIG. 8 is a cut-away perspective of the device showing a chemical composition in combination with a metallic activator according to one embodiment of the invention.

In the case of metallic activators (or initiators), the activator is positioned within the liquid ingredient of the chemical composition and the initiation of the thermal reaction occurs upon operation of the metallic activator. Metallic activators can be in the form of a flexible disc which when flexed initiates crystallization of a solution. This, in this embodiment, the ingredients of the chemical composition are not physically separated from one another prior to use as in the case of pouch structures and the like. FIG. 8 illustrates a device containing a metallic activator 60 located within the containment 12 of the device 10 in contact with a liquid ingredient 19. The metallic activator used can be placed in the device in a substantially fixed position or, alternatively, a free-moving, unfixed manner.

The device of the invention can contain a chemical composition, physical separation means, or combination thereof, which is structured to permit either complete activation of the device in a single use or, alternatively, partial activation of the device allowing for multiple or prolonged use of a single device. Partial activation can be accomplished by rupturing only some of the pouches of the device, for example.

The resulting fluid within the device is permitted to flow in an unrestricted manner throughout the interior of the containment between the inner peripheral base portion and outer peripheral portion of the device, while the discrete attachment areas do not significantly inhibit the flow and maintain the overall nest configuration of the device during its use. The movement or migration of the fluid in the device upon application of weight thereon help conform the device to the user's own contours and geometry, thereby increasing the thoroughness and efficiency of thermal effect on the user's body.

The temperature and time period of thermal effect can vary according to the particular chemical composition used and the patient's needs. In general, the device by virtue of the activated chemical composition produces a temperature for a time period sufficient to render a thermal effect. The thermal effect can be either a cooling or heating thermal effect. In the case of a device intended for normal infant care, the device preferably creates a heating or warming effect. In one embodiment, the chemical composition provides a thermal effect having a temperature within the range of from about 102° F. to about 108° F. The time period of thermal effect can vary. In one embodiment, the time period of thermal effect lasts for approximately 2 hours.

The device of the invention permits the application of thermal therapy in conformance with the patient's own geometry by accommodating the application of weight without adversely affecting the effectiveness or function of the device during its use. In addition to the geometrical accommodation of the device to the patient, the internal flow of fluid within the device is unrestricted by the discrete attachment areas, thereby enabling rapid conformation of the device to the patient's body. When used in infant care, the nest configuration provides a relatively comfortable place for an infant to rest and assists in maintaining the infant in a generally constant position.

As seen in FIG. 6, the device in this particular embodiment is first folded along an axis transverse to the length of at least one pouch 40 to initiate the thermal reaction of the chemical composition inside the device. The infant, for example, is then placed on the device and positioned appropriately within the nest configuration. The weight of the infant thereon distributes the fluid within the device in such a manner that the device conforms to the infant's own geometry and produces a more thorough thermal effect while still maintaining the nest configuration of the entire device and the position of the infant thereon.

Industrial Applicability

The device of the invention can be used in a variety of medical and domestic applications, namely medical or domestic infant or neonatal care, wherein the combined features of thermal therapy or treatment and physical comfort are desired. The device is transportable, easy to use (activate) and store, and can be disposable.

The invention herein has been described in detail herein with reference to various specific and preferred embodiments and techniques. However, it should be understood by one of ordinary skill in the art that many variations and modifications can be made without departing from the spirit and scope of the invention.

We claim:

1. A device for providing thermal treatment comprising:
    a) a containment having upper and lower sides and space therebetween, said upper and lower sides being composed of materials different from one another,
    b) a chemical composition adapted for providing a thermal effect containedwithin said space;
    c) discrete attachment areas connecting the upper and lower sides within the perimeter of the device, said attachment areas being centrally located so as to define an inner peripheral base portion and outer peripheral portion of the device; and wherein the device has a nest configuration and is adapted to conform to a body upon application of weight thereon.

2. The device according to claim 1 wherein the containment is composed of a flexible material which is impervious to fluid.

3. The device according to claim 2 wherein the material is a polymeric material.

4. The device according to claim 2 which further comprises a surface layer laminated to said containment material.

5. The device according to claim 4 wherein the surface layer is composed of a soft, non-abrasive material.

6. The device according to claim 5, wherein the discrete attachment areas make up less than about 3% of the surface area of the upper and lower sides of the device.

7. The device according to claim 2 wherein the material is transparent.

8. The device according to claim 1 wherein the containment is composed of a single layer of material.

9. The device according to claim 1 wherein the containment is composed of multiple layers of material.

10. The device according to claim 1, wherein the discrete attachment areas make up less than about 10% of the surface area of the upper and lower sides of the device.

11. The device according to claim 1, wherein the device contains at least four centrally located discrete attachment areas positioned only in the area between the inner peripheral base portion and outer peripheral portion.

12. The device according to claim 11 wherein the device contains four centrally located discrete attachment areas.

13. The device according to claim 1 wherein the discrete attachment areas are formed using a technique selected from the group consisting of heat sealing, ultrasonic sealing, and chemical adhesion techniques.

14. The device according to claim 1 wherein the overall shape of the device is selected from the group consisting of ovoid, circular, square and rectangular shapes.

15. The device according to claim 14 wherein the overall shape of the device is rectangular.

16. The device according to claim 1 wherein the chemical composition is adapted to provide a thermal effect inn a controllable manner and provide an amount of fluid within the containment sufficient to afford conformability of the device to the user.

17. The device according to claim 16 wherein the fluid is permitted to flow in a unrestricted manner throughout the interior of the containment between the inner peripheral base portion and outer peripheral portion of the device.

18. The device according to claim 16 wherein the chemical composition comprises ingredients which are physically separated.

19. The device according to claim 18 wherein one of the ingredients is contained within at least one rupturable pouch.

20. The device according to claim 19 wherein a solid ingredient is contained within a pouch and a liquid ingredient is surrounding the pouch within the interior of the containment.

21. The device according to claim 19 wherein a liquid ingredient is contained within a pouch and a solid ingredient is located outside of the pouch within the containment.

22. The device according to claim 19 wherein at least one rupturable pouch is located within the inner peripheral base portion of the device.

23. The device according to claim 19 wherein at least one rupturable pouch is located within the outer peripheral portion of the device.

24. The device according to claim 16 wherein the chemical composition comprises a phase change formulation.

25. The device according to claim 24 wherein the phase change formulation comprises an ingredient selected from the group consisting of sodium thiosulphate pentahydrate, sodium acetate trihydrate, and combinations thereof.

26. The device according to claim 24 wherein the phase change formulation comprises a metallic activator.

27. The device according to claim 16 wherein the chemical composition comprises a solute with solvent combination.

28. The device according to claim 27, wherein the solute with solvent combination comprises water and a chemical activator selected from the group consisting of potassium permanganate, calcium chloride, magnesium sulfate, calcium magnesium sulfate, sodium acetate, and combinations thereof.

29. The device according to claim 16, wherein the chemical composition comprises a composition adapted to release or absorb thermal energy.

30. The device according to claim 29, wherein the chemical composition comprises a thermal gel.

31. The device according to claim 30 wherein the thermal gel comprises water and a hydrophilic polymer selected from the group consisting of hydrogels, starches, cellulosics, and silica gels, and combinations thereof.

32. The device according to claim 1 wherein said chemical composition thermal effect produces a temperature for a time period sufficient to render a thermal effect to the user.

33. The device according to claim 32 wherein the thermal effect is exothermic and generates heat.

34. The device according to claim 33 wherein the temperature ranges from about 102° F. to about 108° F.

35. The device according to claim 33 wherein the thermal effect is produced for a period of approximately two hours.

36. The device according to claim 1 wherein the device has dimensions which accommodate an infant's body.

37. A method of warming an infant using the device for providing a thermal effect according to claim 1, comprising:
    a) initiating the thermal reaction of the chemical composition adapted for providing a thermal effect;
    b) placing an infant on the upper side of said device; and
    c) applying the weight of the infant onto the device so as to permit the device to conform to the infant's body.

* * * * *